United States Patent [19]

Barch

[11] Patent Number: 4,610,789

[45] Date of Patent: Sep. 9, 1986

[54] FILTRATION CARTRIDGE AND REACTOR

[75] Inventor: Herbert W. Barch, Natrona Heights, Pa.

[73] Assignee: PPG Industries, Inc., Pittsburgh, Pa.

[21] Appl. No.: 725,872

[22] Filed: Apr. 22, 1985

[51] Int. Cl.$^4$ .................................................. B01D 13/00
[52] U.S. Cl. .................................. 210/321.4; 210/405; 210/450; 210/456; 210/500.23; 210/500.26
[58] Field of Search ............... 210/321.1, 321.2, 321.3, 210/321.4, 405, 456, 500.2, 450

[56] References Cited

U.S. PATENT DOCUMENTS 4,210,536  7/1980  Coplan et al. ...................... 210/321.1

*Primary Examiner*—Frank Sever
*Attorney, Agent, or Firm*—John E. Curley

[57] ABSTRACT

A filter cartridge is structured of a filtration mat assembly wrapped or rolled about a central distribution tube. The filtration mat includes a plurality of hollow porous fiber strands carried by a fluid permeable sheet. Once the mat has been wrapped about the porous central distribution tube, both ends of the mat and distribution tube are firmly embedded in end caps. The central distribution tube is comprised of two tube segments which are telescopingly connected. Shrinkage and contraction or swelling and elongation of the mat's fibers cause the end caps to move toward or away from each other. This movement of the end caps is able to occur due to the ability of the telescoping central distribution tube to decrease or increase in length.

16 Claims, 2 Drawing Figures

FILTRATION CARTRIDGE AND REACTOR

FIELD OF THE INVENTION

The present invention is directed generally to a filtration cartridge assembly. More particularly, the present invention is directed to a filtration cartridge utilizing a filter mat assembly including a plurality of porous glass fiber strands. Most specifically, the present invention is directed to a filtration cartridge having a telescoping, porous, central distribution tube firmly embedded in end caps. The distribution tube is an open weave filament wound member about which the filter mat assembly, which includes a plurality of porous glass fiber strands and fluid permeable sheets, is rolled or wrapped during assembly of the filtration cartridge. The ends of the distribution tube, porous strands, and permeable sheets are then securely embedded in spaced end caps. Since the distribution tube is telescopic, it allows the end caps to move toward or away from each other in accordance with elongation or contraction of the porous glass fiber strands. Such movement of the end caps prevents breakage or crushing of the porous strands.

DESCRIPTION OF THE PRIOR ART

In many filtration processes, membranes are utilized to filter various components of fluid systems. For example, membranes are used to separate gas components from each other in gaseous streams containing multiple gases, to separate various dissolved components in liquid solutions from each other and to selectively permit certain ions in a solution to pass across a membrane while blocking others. Membranes are also utilized to a great extent to immobilize proteins, enzymes and cells. The enzymes, so immobilized are used as catalysts to increase reaction rates or to convert materials in solution from one form to another. Membranes are also utilized in various applications to trap or immobilize living cells within a substrate forming the membrane.

In general, membranes of various types have been employed for these purposes. In the electrolysis field, for example, polymer sheet membranes which are selectively permeable to alkali metal ions have been utilized. Porous glass beads have also been employed in many processes for the purpose of immobilizing enzymes for use in other chemical processes. Organic fibers have also been utilized in many applications, for example, the dialysis of blood. These organic fibers have been utilized in the hollow and porous stage where the material to be purified, in this case blood, is passed through a hollow organic fiber and is purified by enriching it in oxygen and depleting it of waste materials through the pores.

A mat structure useful in membrane filtration is set forth in co-pending U.S. patent applications, Ser. No. 636,755, entitled "Novel Mat Structure", filed Aug. 1, 1984, and assigned to the assignee of the subject application. As is set forth in greater detail in that application, whose disclosure is incorporated herein by reference, there are disclosed mats utilizing glass fibers in the form of fibers, glass fiber strands, which comprise groups of glass fibers, and glass fiber rovings which comprise groups of glass fiber strands. The glass fibers used to produce the mats whether they are used as fibers, strands or rovings, are porous glass fibers, hollow glass fibers, or hollow glass fibers, which are also porous.

Mats made from these fibers have been utilized in forming filtration cartridges for use in filtration reactors for gas and/or liquid separations, for reverse osmosis and ultrafiltration systems, as a carrier for cell cultures in reactors requiring large flat surface areas for cell growth, as elements in systems designed for the immobilization of proteins and enzymes, as blood dialysis membranes and other such systems. The number of fibers used to prepare the mats provide hundreds of thousands to millions of individual glass fibers in a form readily adaptable for use in various filtration and immobilization reactors. A cartridge and reactor assembly utilizing these mat structures is set forth in co-pending U.S. patent application Ser. No. 637,233, entitled "Novel Cartridge and Reactor", filed Aug. 2, 1984, and assigned to the assignee of the present application. The disclosure of that application is incorporated herein by reference.

As is disclosed in U.S. patent application Ser. No. 637,233, filed Aug. 2, 1984, and directed to the cartridge and reactor, the mat structure set forth in U.S. patent application Ser. No. 636,755, filed Aug. 1, 1984, is wrapped or rolled about a central elongated hollow and porous distribution tube with the ends of the mat being embedded in end caps through which at least one end of the central distribution tube slideably passes. This sliding cooperation between the end cap or casing and the distribution tube is necessary to compensate for elongation or contraction of the porous strands placed in the mat structure.

While the structure of the distribution tube and end casing set forth in the previous application has proved successful, the structure of the filtration cartridge and reactor in accordance with the present invention is believed to result in a filter cartridge even better able to compensate for porous strand elongation and contraction.

SUMMARY OF THE INVENTION

It is an object of the present invention to provide a filtration cartridge and reactor.

Another object of the present invention is to provide a filtration cartridge utilizing a plurality of elongated, porous, glass fiber strands.

A further object of the present invention is to provide a filtration cartridge having a mat of glass fiber strands and fluid permeable sheets.

Yet another object of the present invention is to provide a filtration cartridge having a filtration mat wrapped about a central distribution tube.

Still a further object of the present invention is to provide a filter cartridge having a central, porous distribution tube whose length is telescopingly adjustable.

Yet still another object of the present invention is to provide a filtration cartridge having ends of the filtration mat and of the telescoping distribution tube firmly embedded in end caps or casings.

As will be discussed in greater detail in the description of the preferred embodiment which is set forth hereinafter, the filter cartridge assembly in accordance with the present invention comprises a mat of a plurality of hollow, porous, glass fiber strands supported on one or more fluid permeable sheets and wrapped or rolled about a central porous, telescoping distribution tube. The ends of the distribution tube, porous strands, and fluid permeable sheets are firmly embedded in upper and lower spaced end caps or casings. As often happens, the porous strands may elongate or contract, either when porosity is imparted to them in the assembled cartridge, or as the strands and fibers swell as well as for other reasons. The telescoping central distribution tube that is firmly embedded in the end caps of the cartridge, allows these end caps to move toward or away from each other in response to strand contraction or elongation. This freedom of motion prevents stretching and breakage of the fiber strands and also eliminates compression and crushing of the strands.

The central distribution tube may be fabricated as a one piece open weave filament tube which is then severed generally at the midpoint of its length. A portion of the tube adjacent one end of one of the severed portions may be reduced in diameter so that it will fit inside the complimentary member. The reduced diameter portion of one segment of the tube terminates in a shoulder that will abut the end of the second segment and hence limits the amount of shortening that the distribution tube can undergo. This telescoping length change amounts is predetermined by the amount of strand fiber extension or contraction expected. Since the central porous distribution tube is casted directly to the upper and lower end caps of the filtration cartridge, there are no sealing problems or looseness between the two. The positive, firm embedding of the distribution tube in the end caps provides a stable, durable filtration cartridge that is superior to prior devices.

BRIEF DESCRIPTION OF THE DRAWINGS

While the novel features of the filtration cartridge and reactor in accordance with the present invention are set forth with particularity in the appended claims, a full and complete understanding of the invention may be had by referring to the description of the preferred embodiment as set forth hereinafter, and as may be seen in the accompanying drawings, in which:

DESCRIPTION OF THE PREFERRED EMBODIMENT

Figure 1:
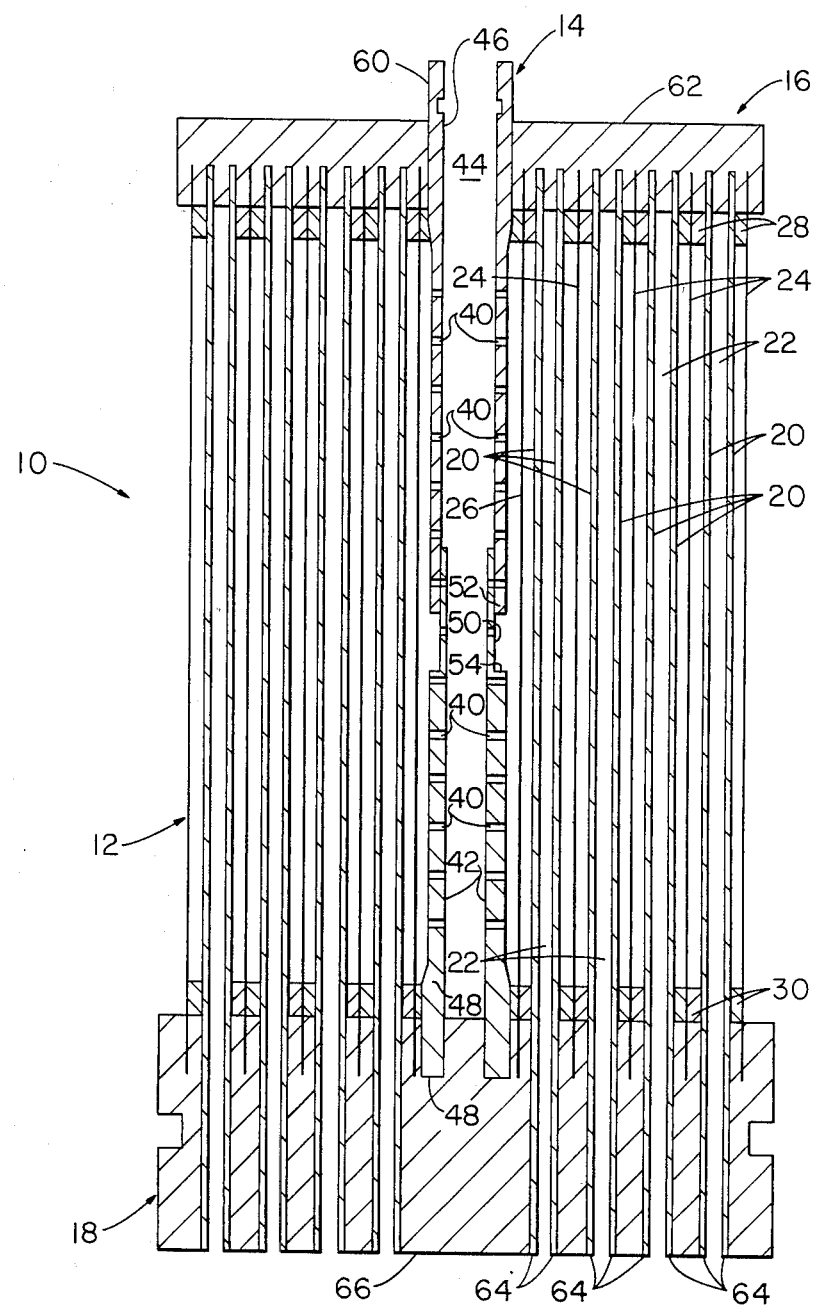
FIG. 1 is a side elevation view, partly in section of a filtration cartridge in accordance with the present invention.

Referring initially to FIG. 1, there may be seen generally at 10 a filtration cartridge in accordance with the present invention. Cartridge 10 is comprised generally of a filtration mat assembly, generally at 12, which is wrapped or rolled about a central, porous, telescoping distribution tube generally at 14. Mat assembly 12 and distribution tube 14 are cast or embedded at their ends in upper and lower and caps or casings generally at 16 and 18, respectively.

Filtration mat assembly 12 is of the type set forth in detail in co-pending U.S. patent application Ser. No. 636,755, filed Aug. 1, 1984, and entitled "Novel Mat Structure". While a detailed description of mat assembly 12 will not be repeated here, the mat assembly is comprised generally of a plurality of porous elongated glass fiber strands 20 each of which may be formed by a plurality of hollow fibers (not shown here for clarity but shown in detail in the above referenced application). Each strand 20 is hollow and has a axially extending bore of lumen 22 which again is shown somewhat schematically in FIG. 1. A first fluid permeable sheet 24 is interposed between the concentric rings of spirals of elongated strands 20, and a second fluid permeable sheet 26 is positioned between the central distribution tube 14 and the radially innermost ring of elongated strands 20. An upper binding strip 28 and a lower binding strip 30, which are formed of an adhesive material, are used to cohesively bond the adjacent hollow porous strands 20 to each other and to the fluid permeable sheets 24 and 26. In assembling the mat assembly 12, the hollow porous strands are placed on the first fluid permeable sheet 24 in a generally side by side parallel array. The upper and lower binding strips 28 and 30 are put in place transversely across the strands 20, and the second porous sheet 26 is placed at one end of the mat generally perpendicularly to the binding strips 28 and 30. The central distribution tube 14 is then placed adjacent the end of the mat assembly 12 at the end of the mat at which the second permeable sheet 26 is located. The mat assembly 12 is then wound or wrapped about the central distribution tube 14 generally in the nature of a jelly roll to arrive at the configuration shown in FIG. 1.

Central distribution tube, generally at 14, is an open weave type filament wound tube having a plurality of pores or apertures 40 formed in its walls 42. A central bore 44 extends the length of distribution tube 14 with the axis of bore 44 being generally aligned with the bores or lumens 22 of the numerous hollow porous strands 20. Distribution tube 14 is comprised of an upper tube segment 46 and a lower tube segment 48 with these tube segments being in telescoping cooperation. As may be seen in FIG. 1 an upper portion 50 of lower tube segment 48 is reduced in diameter so that its outer diameter is slightly less than the inner diameter of upper tube segment 46. Thus the upper end 50 of lower tube segment 48 is positionable within the lower end 52 of upper tube segment 46 of distribution tube 14. A shoulder 54 is formed on lower tube segment 48 at the termination of the reduced diameter upper portion 50 of lower tube segment 48. This shoulder cooperates with lower end 52 of upper tube segment 46 to limit the minimum length which central distribution tube 14 can telescope down to. It will be apparent that distribution tube 14 can be formed of upper and lower segments 46 and 48 of equal length as seen in FIG. 1, or of unequal lengths, if desired. Further, upper tube segment 46 could telescope within lower tube segment 48 as opposed to the arrangement shown in FIG. 1.

Once the filtration mat assembly 12 has been wrapped or rolled about central distribution tube 14, the upper and lower end caps or casings 16 and 18 are cast in place. These end caps 16, 18 are cast of a suitable material such as a catalytic or thermoset curable resin. Once the ends of the filtration mat 12 and distribution tube 14 are cast in the end caps 16, 18, the unitary filtration cartridge 10 has been assembled. Upper and lower end caps 16 and 18 are both generally similar in that they are both generally disk shaped. An upper end portion 60 of upper distribution tube segment 46 passes upwardly through an upper surface 62 of upper end cap 16. Upper ends of hollow strands 20 and first and second fluid permeable sheets 24 and 26 are embedded within upper end cap 16. Upper binding strip 28 serves to prevent migration of the resin forming upper end cap 16 downwardly during casting.

Lower end cap 18 is also generally disk-shaped. However, in contrast to upper end cap 16, in lower end cap 18 lower ends of 64 of hollow strands 20 pass through to a lower surface 66 of lower end cap 18. A lower end portion 68 of lower segment 48 of distribution tube 48 is cast in lower end cap 18. Lower binding strip 30 prevents resin migration during casting of the filter cartridge assembly.

As has been alluded to previously, the porosity of hollow strands 20 is often chemically adjusted after the filter cartridge 10 has been formed. This is apt to cause the strands 20 to contract or shorten. Although the ends of distribution tube segments 46 and 48 are firmly bonded in end caps 16 and 18, respectively, since the tube assembly is telescopingly adjustable in length, this contraction of the strands 20 can be readily accommodated since distribution tube 14 is capable of becoming shorter. Similarly, various uses to which cartridge assembly 10 may be placed cause the strands 20 to swell and expand or elongate. Again, the telescoping construction of central distribution tube 14 allows the end caps 16 and 18 to move apart from each other. The telescoping structure of central distribution tube 14 allows its ends 60 and 68 to be firmly bonded in upper and lower end caps 16 and 18 thereby forming a unitary filter cartridge 10 while at the same time providing a means to allow strand contraction or elongation. Without the telescoping central distribution tube 14, the strands 20 would be apt to break as they tried to contract or become crushed and compacted as they tried to swell or elongate.

Figure 2:
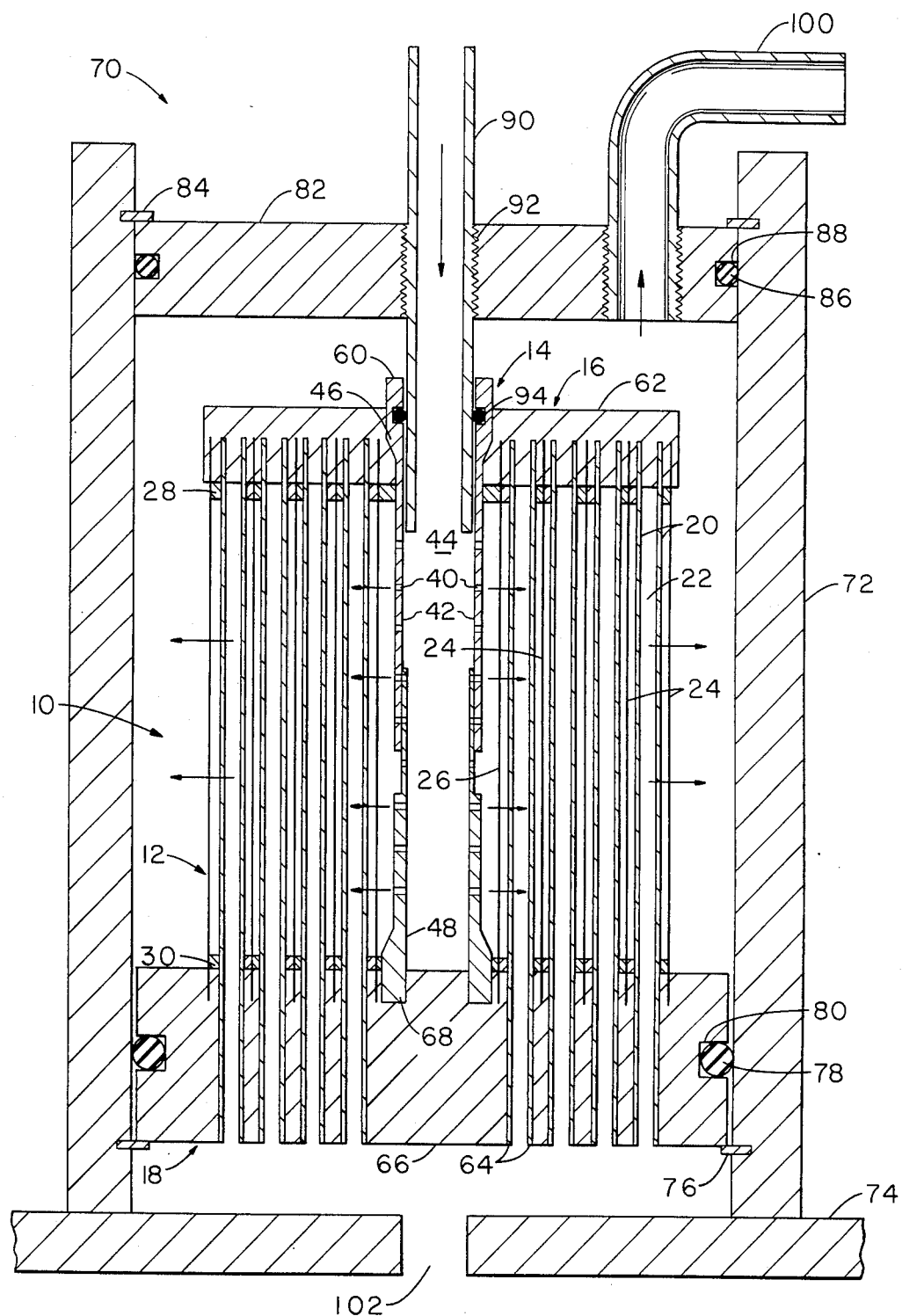
FIG. 2 is a side elevation view, partly in section of a reactor in accordance with the present invention and utilizing the filtration cartridge shown in FIG. 1.

Turning now to FIG. 2, there may be seen generally at 70 a reactor assembly which utilizes the filtration cartridge 10 of the present assembly. Reactor assembly 70 is set forth in detail in co-pending application Ser. No. 637,233, filed Aug. 2, 1984, entitled "Novel Cartridge and Reactor", and assigned to the assignee of the subject application. Reactor assembly 70 includes a generally tubular or cylindrical casing 72 having a lower end plate 74 securely attached thereto. Cartridge assembly 10 is placed within tubular casing 72 with the bottom 66 of lower end cap contracting a lower snap ring 76. A suitable sealing O-ring gasket 78 is provided in a circumferential groove 80 in the side wall of lower end cap 18. Once cartridge 10 is in place within tubular casing 72, an upper end plate 82 is put in the open upper end of cylinder 72 and is held in place by a snap ring 84. An O-ring gasket 86 is positioned in a cooperatively shaped circumferential ring on the side wall of upper end plate 82. A fluid inlet line 90 is screwed into a threaded bore 92 in upper end plate 82 and passes down into the open upper end 60 of upper tube segment 46 of distribution tube 14. An O-ring seal 94 is secured in the upper end 60 of upper tube segment 46. This provides a fluid tight seal while not restricting movement of telescoping central distribution tube 14. A fluid outlet line 100 is also attached to upper end plate 82.

In usage, fluid passes through inlet line 90 and into central, telescoping distribution tube 14. The fluid then passes radially outwardly through apertures 40 in tube wall 42 and through the second fluid permeable sheet 26 which is interposed between the distribution tube 14 and the first ring of hollow porous strands 20 and acts to protect the strands from damage by dissipating fluid flow forces. Since the lower end 68 of central distribution tube 14 is sealed in lower end cap 18, all the fluid entering cartridge 10 will pass into the filter mat assembly 12. Any material that can, will pass through the porous walls of the hollow strands 20 and down through the interior bores or lumens 22 in strands 20 to their lower ends 64 to exit through a discharge opening 102 in the lower end plate 74. Materials not passing through the hollow strands 20 will move radially outwardly in the direction indicated by the arrows in FIG. 2, and will eventually leave reactor assembly 70 through outlet line 100. Any swelling or shrinkage of strands 20 that may be experienced during usage of cartridge 10 in reactor 70 will cause end caps 16 and 18 to move with respect to each other. The telescoping central distribution tube 14, which is firmly embedded in end caps 16 and 18, will allow such movement to occur. Thus breakage or crushing of the hollow strands 20 will be essentially eliminated.

While a preferred embodiment of a filtration cartridge and reactor in accordance with the present invention has been fully and completely described hereinabove, it will be obvious to one of skill in the art that a number of changes in, for example, the size of the cartridge, the materials used for the hollow strands, the materials used for the end caps, the shape of the reactor, and the like could be made without departing from the true spirit and scope of the invention which is to be limited only by the following claims.

I claim:

1. A hollow fiber filter cartridge usable in a reactor, said filter cartridge comprising:
    a filtration mat assembly including a plurality of generally parallel elongated hollow strands and at least a first fluid permeable sheet;
    a porous central distribution tube about which said filtration mat assembly is wrapped;
    spaced upper and lower end caps, upper and lower end portions of said central distribution tube and said filtration mat assembly being firmly embedded in said upper and lower end caps respectively; and
    means for adjusting the length of said tube responsive to movement of said end caps toward or away from each other and in amounts sufficient to preclude breaking said strands upon stretching or crushing said strands upon compression.

2. The cartridge of claim 1 wherein said central distribution tube is comprised of an upper distribution tube segment and a lower distribution tube segment.

3. The cartridge of claim 2 wherein said means for varying the length of said central distribution tube is a telescoping engagement of said upper and lower distribution tube segments.

4. The cartridge of claim 3 wherein a first of said tube segments includes a reduced diameter end portion which is receivable within a second of said tube segments to effect said telescoping engagement.

5. The cartridge of claim 4 wherein said first tube segment includes a shoulder at the termination of said reduced diameter end portion, said shoulder limiting the telescoping contraction of said central distribution tube.

6. The cartridge of claim 2 wherein a first of said tube segments is firmly embedded in, and passes through, a first one of said end caps, and further wherein a second of said tube segments is firmly embedded in, and terminates in, a second one of said end caps.

7. The cartridge of claim 1 wherein said strands are glass strands.

8. A hollow fiber filter cartridge usable in a reactor, said filter cartridge comprising:
    a filtration mat assembly including a plurality of generally parallel elongated hollow strands and at least a first fluid permeable sheet;
    a porous central distribution tube about which said filtration mat assembly is wrapped;
    spaced upper and lower end caps, upper and lower end portions of said central distribution tube and said filtration mat assembly being firmly embedded in said upper and lower end caps respectively; and means for adjusting the length of said tube responsive to movement of said end caps toward or away from each other and in amounts sufficient to preclude breaking said strands upon stretching or crushing strands upon compression.

9. The cartridge of claim 8 wherein said central distribution tube is comprised of an upper distribution tube segment and a lower distribution tube segment.

10. The cartridge of claim 9 wherein said means for varying the length of said central distribution tube is a telescoping engagement of said upper and lower distribution tube segments.

11. The cartridge of claim 10 wherein a first of said tube segments includes a reduced diameter end portion which is receivable within a second of said tube segments to effect said telescoping engagement.

12. The cartridge of claim 11 wherein said first tube segment includes a shoulder at the termination of said reduced diameter end portion, said shoulder limiting the telescoping contraction of said central distribution tube.

13. The cartridge of claim 9 wherein a first of said tube segments is firmly embedded in, and passes through, a first one of said end caps, and further wherein a second of said tube segments is firmly embedded in, and terminates in, a second one of said end caps.

14. The cartridge of claim 8 wherein said porous strands are also hollow.

15. The cartridge of claim 14 wherein said strands are glass strands.

16. The cartridge of claim 8 wherein said strands are glass strands.

* * * * *